United States Patent [19]
Guigan

[11] Patent Number: 5,188,583
[45] Date of Patent: Feb. 23, 1993

[54] APPARATUS FOR SEPARATING TWO PHASES OF A SAMPLE OF HETEROGENEOUS LIQUID BY CENTRIFUGING, THE APPARATUS BEING PARTICULARLY SUITABLE FOR SEPARATING PLASMA FROM WHOLE BLOOD

[76] Inventor: Jean Guigan, 5, rue des Ursulines, 75005 Paris, France

[21] Appl. No.: 739,542

[22] Filed: Aug. 2, 1991

[30] Foreign Application Priority Data

Aug. 3, 1990 [FR] France .................. 90 09982

[51] Int. Cl.$^5$ .................................................. B04B 11/06
[52] U.S. Cl. ........................................ 494/43; 494/68; 210/782
[58] Field of Search .................. 494/38, 43, 64, 67, 494/68; 210/782; 422/72, 101; 436/177

[56] References Cited

U.S. PATENT DOCUMENTS

| | | | |
|---|---|---|---|
| 1,002,471 | 9/1911 | Thelitz | 494/67 |
| 2,291,117 | 7/1942 | Strezynski | 494/43 X |
| 3,297,244 | 1/1967 | Hein | 494/43 X |
| 3,825,178 | 7/1974 | Burg | 494/43 X |
| 4,091,089 | 5/1978 | Schlutz | 233/14 R |
| 4,311,585 | 1/1982 | Bergstrom | 494/43 X |
| 4,332,351 | 6/1982 | Kellogg et al. | 494/43 X |
| 4,854,933 | 8/1989 | Mull | 494/38 |
| 4,911,833 | 3/1990 | Schoendorfer et al. | 210/782 |

FOREIGN PATENT DOCUMENTS

| | | | |
|---|---|---|---|
| 2537281 | 6/1984 | France . | |
| 643726 | 9/1950 | United Kingdom | 494/64 |
| 2137537 | 10/1984 | United Kingdom | 494/43 |

Primary Examiner—Frankie L. Stinson
Attorney, Agent, or Firm—Sughrue, Mion, Zinn, Macpeak & Seas

[57] ABSTRACT

The device for separating plasma from a sample of whole blood by centrifuging comprises:

a distributor-divider disposed centrally and provided with n compartments communicating with a sample-receiving well and communicating with one another via notches;

a ring separator including n receptacles communicating with the n compartments and with n outer cells and terminating in an open funnel; and a removable plasma collector fitted onto said funnel.

4 Claims, 7 Drawing Sheets

APPARATUS FOR SEPARATING TWO PHASES OF A SAMPLE OF HETEROGENEOUS LIQUID BY CENTRIFUGING, THE APPARATUS BEING PARTICULARLY SUITABLE FOR SEPARATING PLASMA FROM WHOLE BLOOD

The present invention relates to apparatus for separating two phases of a sample of a heterogeneous liquid by centrifuging, and particularly suitable for separating plasma from whole blood.

BACKGROUND OF THE INVENTION

In the past, a blood sample contained in a tube has either been coagulated or else it has been centrifuged. If centrifuged, the red corpuscles which correspond to substantially 60% (by volume) of whole blood separate from the plasma and collect in the bottom of the tube. An operator then uses a pipette disposed above the red corpuscles to take off the quantity of plasma required for the intended analyses. If the operator is clumsy about the separation zone between the two phases, one or other of the following two situations may arise:

a significant amount of plasma to be collected is lost; or red corpuscles enter the pipette and contaminate the plasma for analysis.

An object of the present invention is to avoid this drawback and to separate plasma automatically from a blood sample without manual intervention and without contamination, and as soon as the sample has been taken, without waiting for coagulation, and to do this at very low cost.

SUMMARY OF THE INVENTION

The present invention provides an apparatus for separating two phases of a sample of heterogeneous liquid by centrifuging, the apparatus being particularly suitable for separating plasma from whole blood, wherein the apparatus comprises a closed assembly about an axis of revolution and comprising:

a distributor-divider disposed centrally and provided with n compartments delimited by radial partitions, the first compartment communicating firstly with the outside via a well for receiving a sample of whole blood and secondly with the second compartment via an overflow, the second compartment similarly communicating with a third via an overflow, and so on to the n-th compartment which does not communicate with the first compartment, all of the overflows being situated at the same height, and said distributor-divider being filled progressively merely under gravity;

a ring separator situated around said distributor-divider and incorporating n receptacles respectively communicating:

with n compartments via respective orifices situated at a height which is significantly greater than that of said overflows to ensure that the blood contained in said compartments pours into said receptacles only under the effect of centrifuging;

via respective restrictions with n outer separation cells for storing red corpuscles, the ratio of the volume to be contained in each cell relative to the volume of said associated compartment being not less than the volume ratio of red corpuscles relative to whole blood, thereby ensuring that the interface between the red corpuscles and the plasma which is established in each cell when centrifuging stops lies below said restrictions;

in between, a common bottom portion narrowing into a funnel; and a removable plasma collector situated centrally beneath said funnel.

The general principle of the above apparatus is to divide the said sample into a plurality of defined quantities such that the separation line between plasma and red corpuscles is also well-determined so to enable automatic collection to be performed.

In addition, said plasma collector includes identity means, with all of the necessary information being recorded at the moment that a sample is taken.

In a variant, said distributor-divider includes an (n+1)th compartment which is open to the outside and intended solely for disposing of any possible excess quantity of said sample of whole blood.

Apparatus of the invention may have a diameter lying in the range about 60 mm to about 70 mm may be made of a plastic that is molded or injected and that is inert relative to blood.

BRIEF DESCRIPTION OF THE DRAWINGS

An embodiment of the invention is described by way of example with reference to the accompanying drawings, in which.

DETAILED DESCRIPTION

Figure 1:
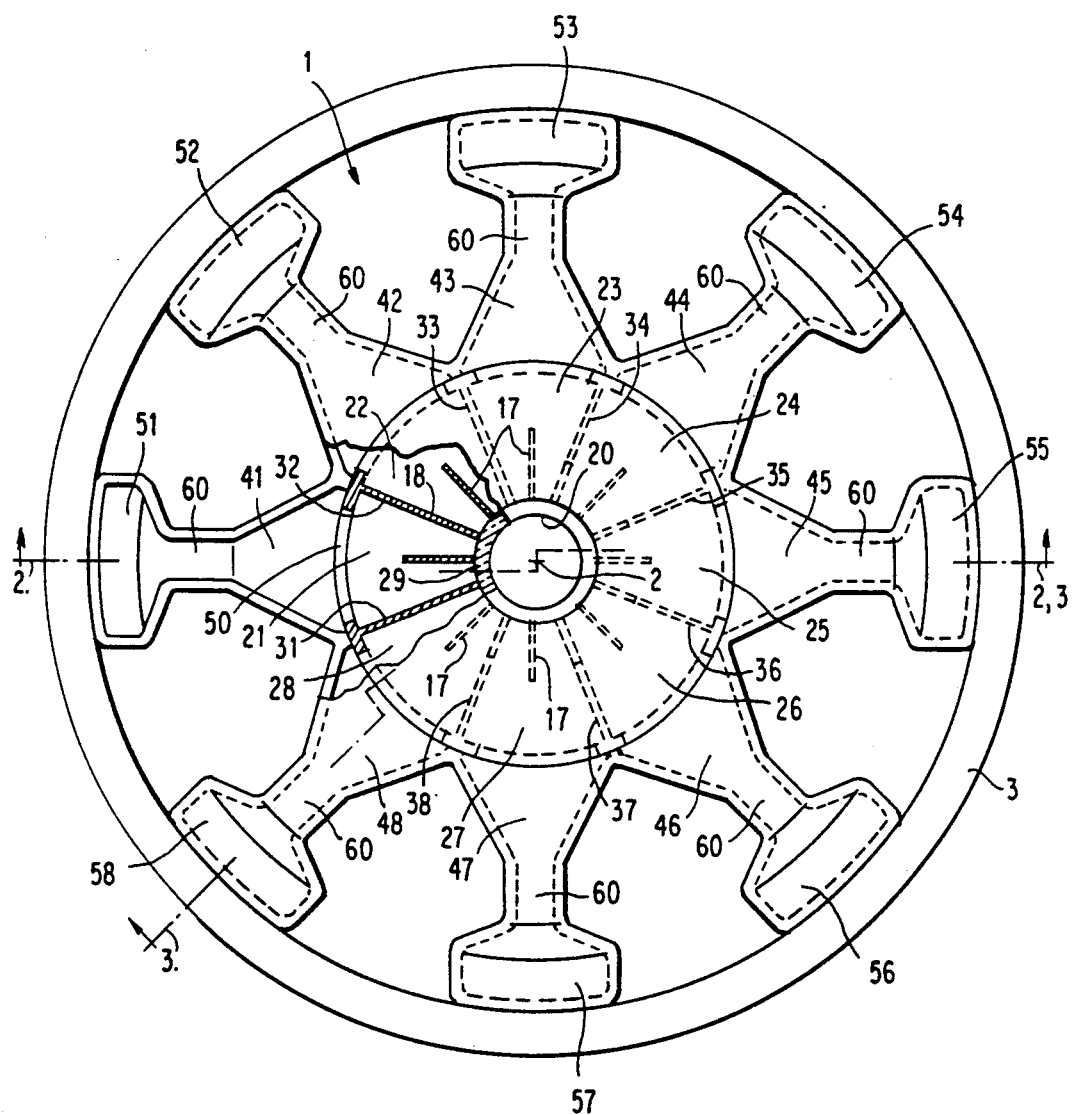
FIG. 1 is a partially cutaway diagrammatic plan view of apparatus of the invention installed on a centrifuge.
Figure 2:
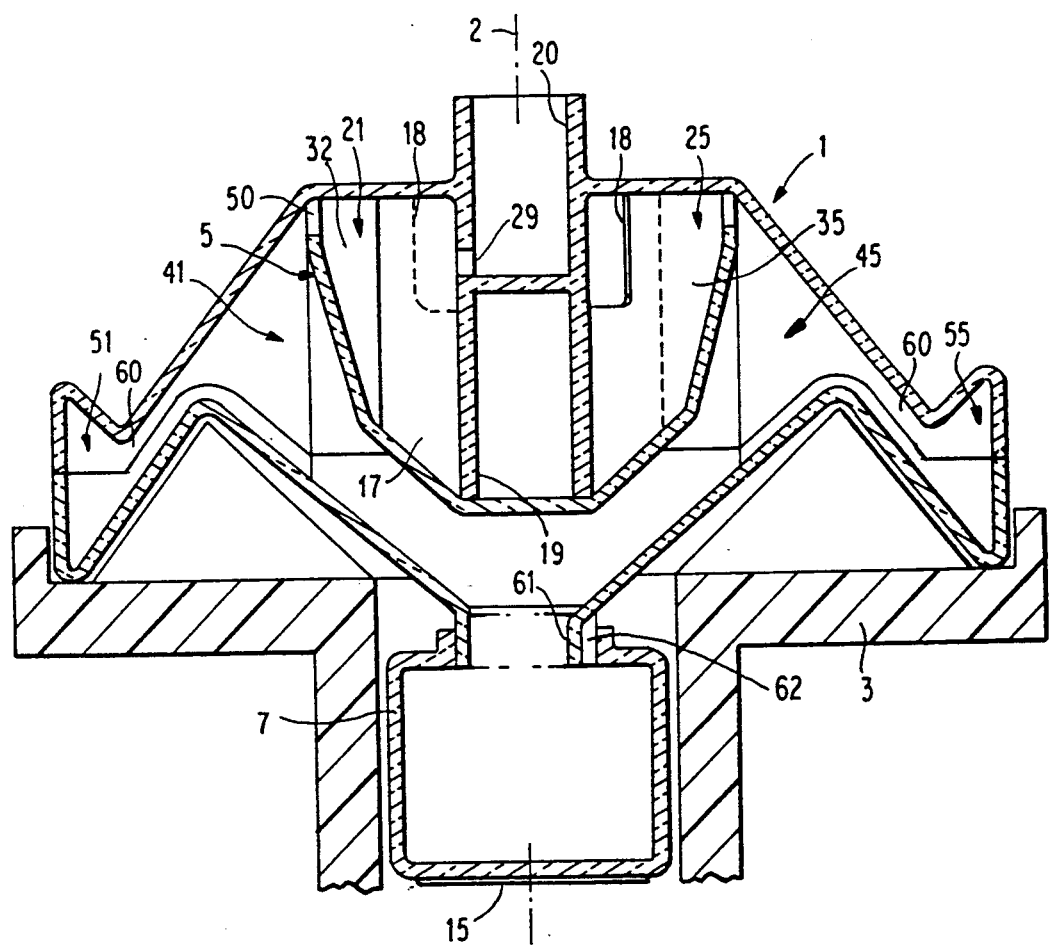
FIG. 2 is a diagrammatic section view on line II—II of FIG. 1.
Figure 3:
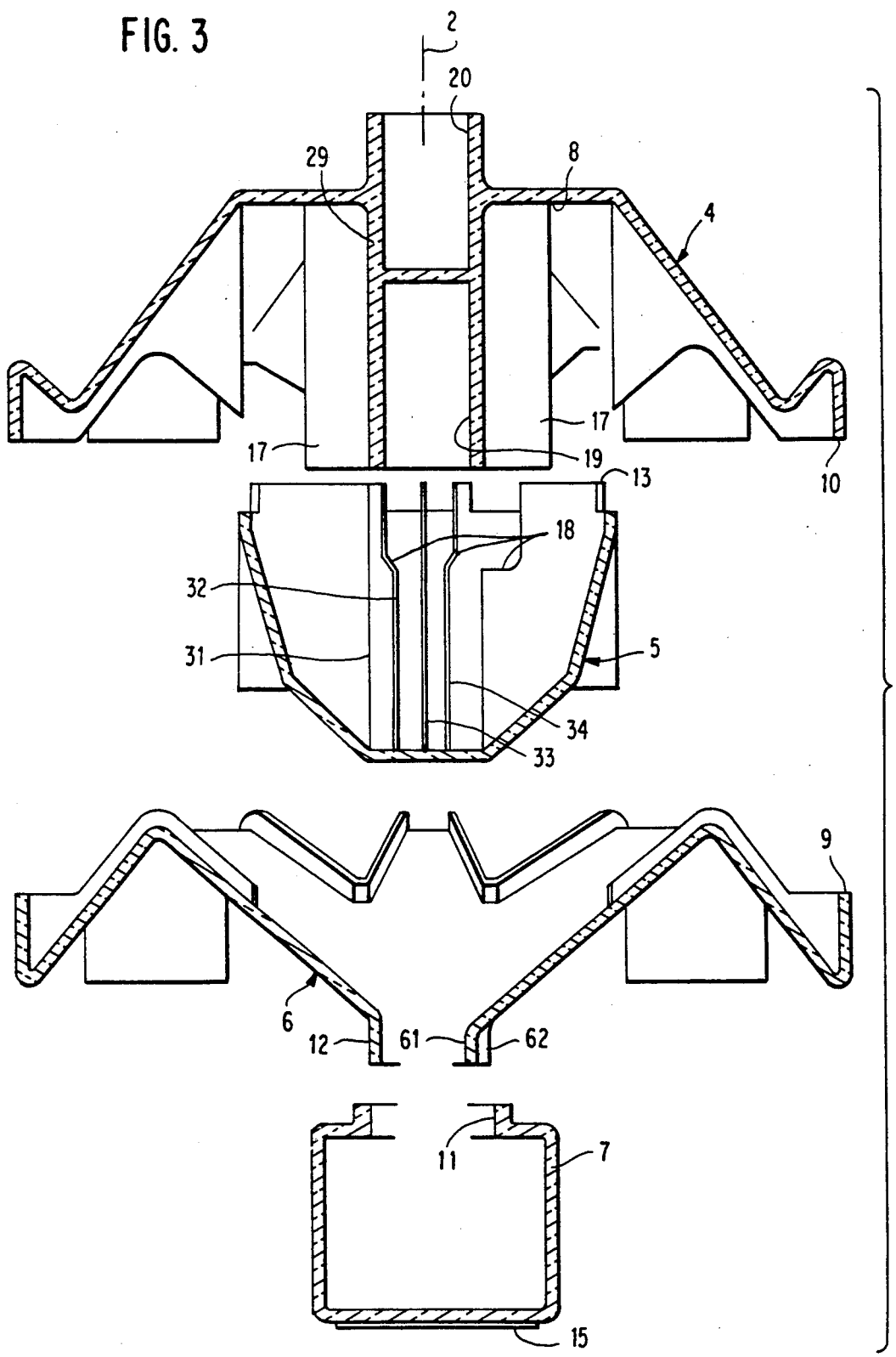
FIG. 3 is a diagrammatic exploded section view on line III—III of FIG. 1.

The apparatus 1 of the invention as shown in FIGS. 1, 2, and 3 has an axis of revolution 2 and it is designed to be installed on a cetrifuge 3.

In outline and without going into detail of the shapes that are defined below, it can be seen that the device 1 may be made up of four parts (see FIG. 3). A top part 4 constitutes a cover and carries on its inside face 8 an intermediate part 5 which is in the form of a cup and which is fixed thereto around its top lip 13 by means of glue or any other appropriate means. The periphery 10 of the top part 4 is fixed to the periphery 9 of a bottom part 6, e.g. by welding, and the central portion of the bottom part is funnel-shaped, leading to an opening 12. A substantially rectangular plasma collector 7 is fitted at 11 onto the opening 12. One of its faces 15 carries the identity of the blood sample to be treated. Any appropriate optical or magnetic means may be considered for this purpose. There is therefore no need to transcribe this identity from the receptacle containing the blood to the receptacle containing the plasma as is the case in prior methods. This constitutes a considerable saving in manual intervention and a considerable gain in security.

The four above-specifiexi parts are made of a plastic which is inert relative to blood. The parts 4, 5, and 6 may be injected whereas the part 7 may be blown. The apparatus 1 advantageously has a diameter lying in the range 60 mm to 70 mm, and a height of about 20 mm. The quantity of plastic required is about 6 grams (g). The dimensions and the weight of the apparatus 1 are such that it is suitable for installing on the turntable of a portable minicentrifuge 3.

Figure 5:
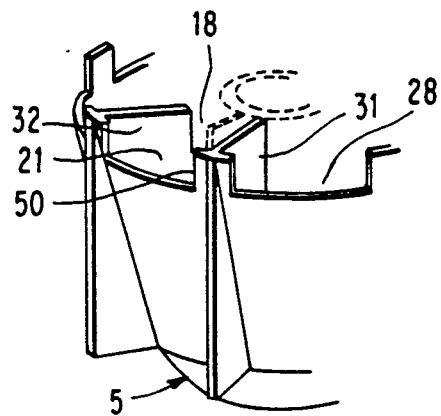
FIG. 5 is a fragmentary perspective view of the distributor-divider of the FIG. 1 apparatus.

As can be seen in FIGS. 1, 2, and 3, the top part 4 and the intermediate part 5 define a whole blood distributor-divider. The part 5 is internally divided into eight compartments 21 to 28 delimited by radial partitions 31 to 38 disposed around a central chimney 19. The first compartment 21 communicates via an opening 29 with a central well 20 for receiving a sample of whole blood. Unlike the partition 31 between the first compartment 21 and the last compartment 28 (see FIGS. 3 and 5), all of the other partitions 32 to 38 have respective notches 18 at the same level for putting the compartment 21 into communication with the compartment 22, and so on, successively to the compartment 28. Numeral 17 references eight radial distribution fins projecting from the outside wall of the central chimney 19.

Figure 7:
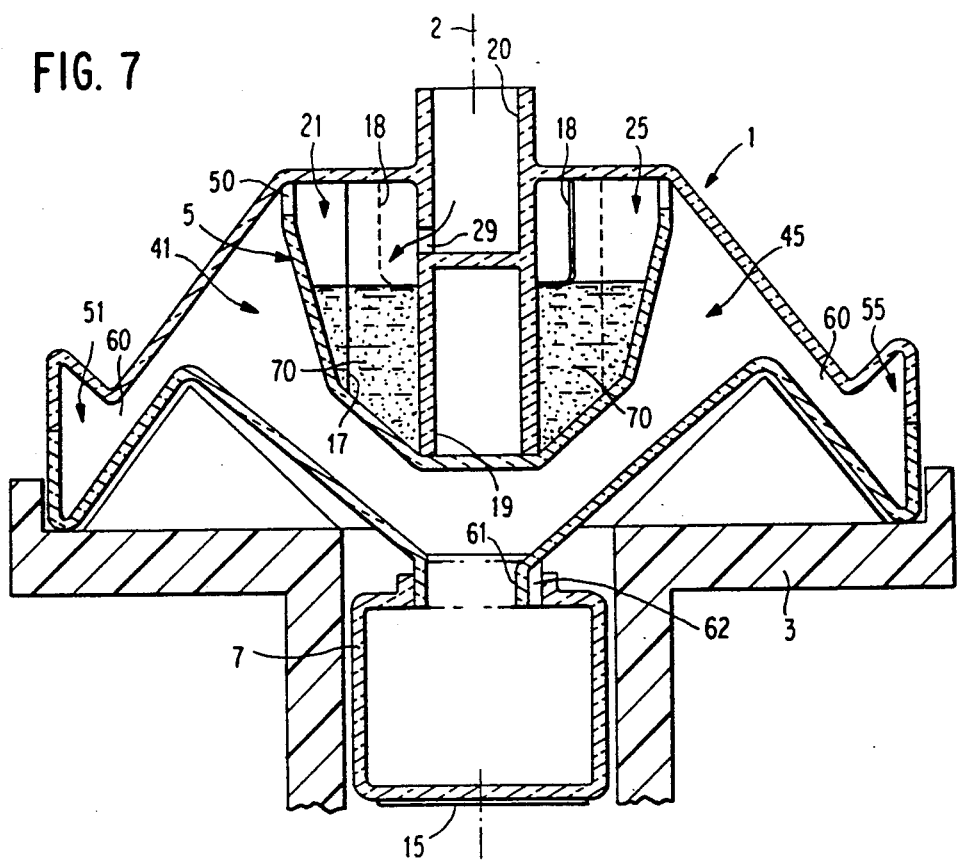
FIGS. 7 to 12 are diagrams showing various stages in the operation of the apparatus of the invention.
Figure 8:
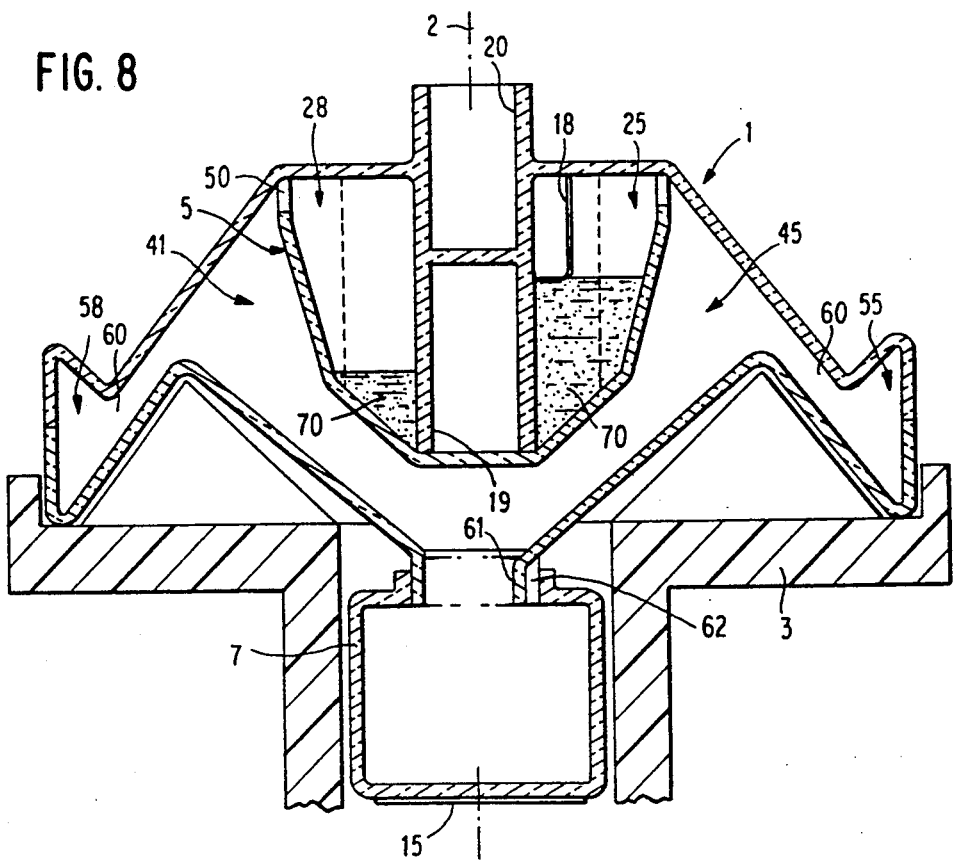
Figure 9:
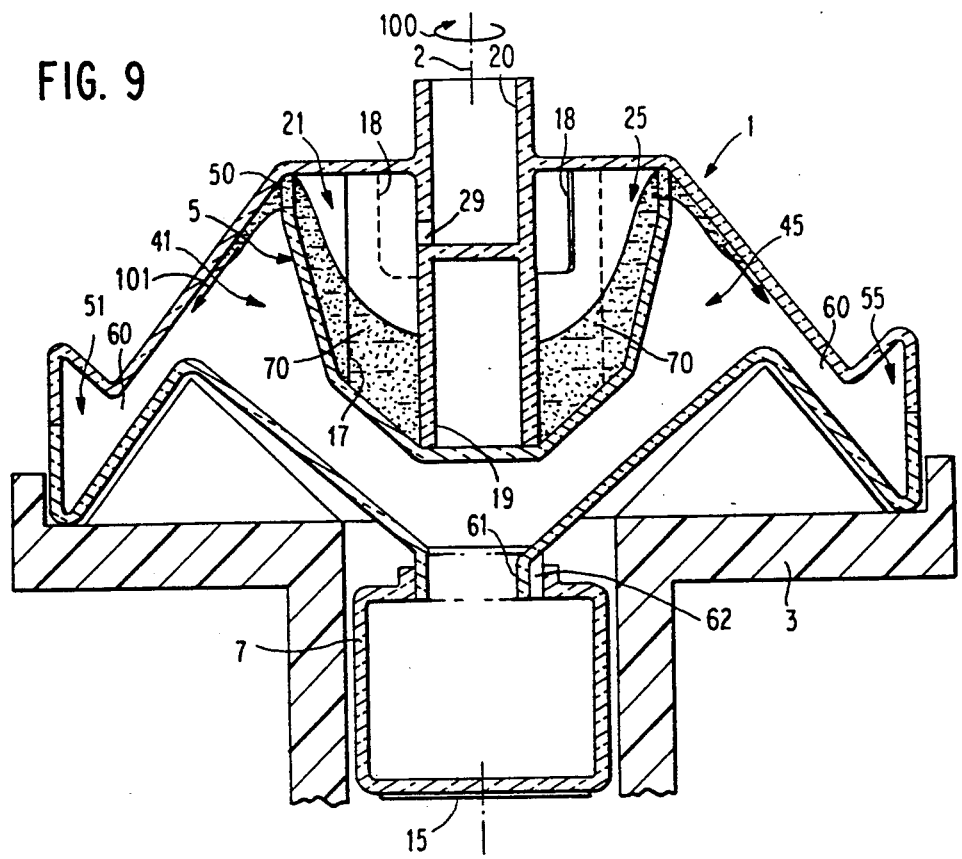

When a whole blood sample 70 is placed in the well 20, the blood 70 flows through the opening 29 into the first compartment 21 until it reaches the level of the notch 18 in the partition 32 constituting an overflow for pouring blood into the second compartment 22, and so on. In most cases, the seven compartments 1 to 22 will be filled under gravity from one compartment to the next, while the compartment 21 will be filled only in part (see FIGS. 7 and 8).

There now follows a description of how the parts 4 and 6 and the outside wall of the part 5 define a separator for separating red corpuscles and plasma.

Figure 4:
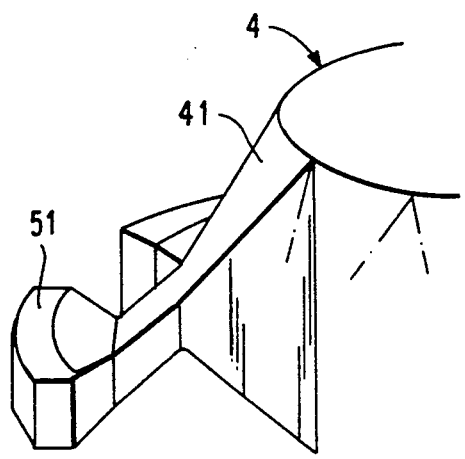
FIG. 4 is a fragmentary perspective view of the top portion of the ring separator of the FIG. 1 apparatus.
Figure 6:
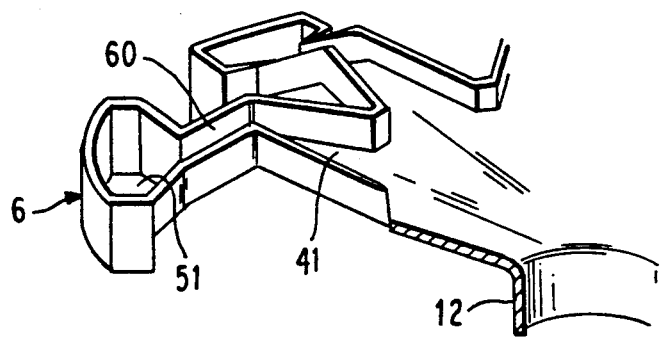
FIG. 6 is a partially cutaway fragmentary perspective view of the bottom portion of the separator of FIG. 4.

This separator is disposed in a ring around the distributor-divider. It is made up of eight receptacles 41 to 48 respectively associated with the compartments 21 to 28 and leading to eight respective outer separation cells 51 to 58 for storing red corpuscles. The receptacle 41 and the cell 51 are taken by way of example and they appear in greater detail in the section of FIG. 2 and in perspective in FIGS. 4 and 6. The receptacle 41 communicates with the compartment 21 via an orifice 50 situated at a height which is considerably higher than the bottom edge of the overflow notch 18. The receptacle 41 is connected by a restriction 60 to the outer cell 51. The volume that can be retained in any one of the outer cells 51 to 58 up to the restriction 60 is not less than 60% of the volume that may be contained in the corresponding compartment 21 to 28. (The value of 60% corresponds substantially to the volume ratio of red corpuscles to whole blood.)

The funnel-shaped common bottom portion of the receptacles 41 to 48 communicates with the above-defined plasma collector 7. The edge of the opening 12 to the funnel has a deformation in the form of a rib 61 (see FIGS. 2 and 3) which co-operates with the lip 11 of the plasma collector 7 to define an air vent orifice 62.

Figure 10:
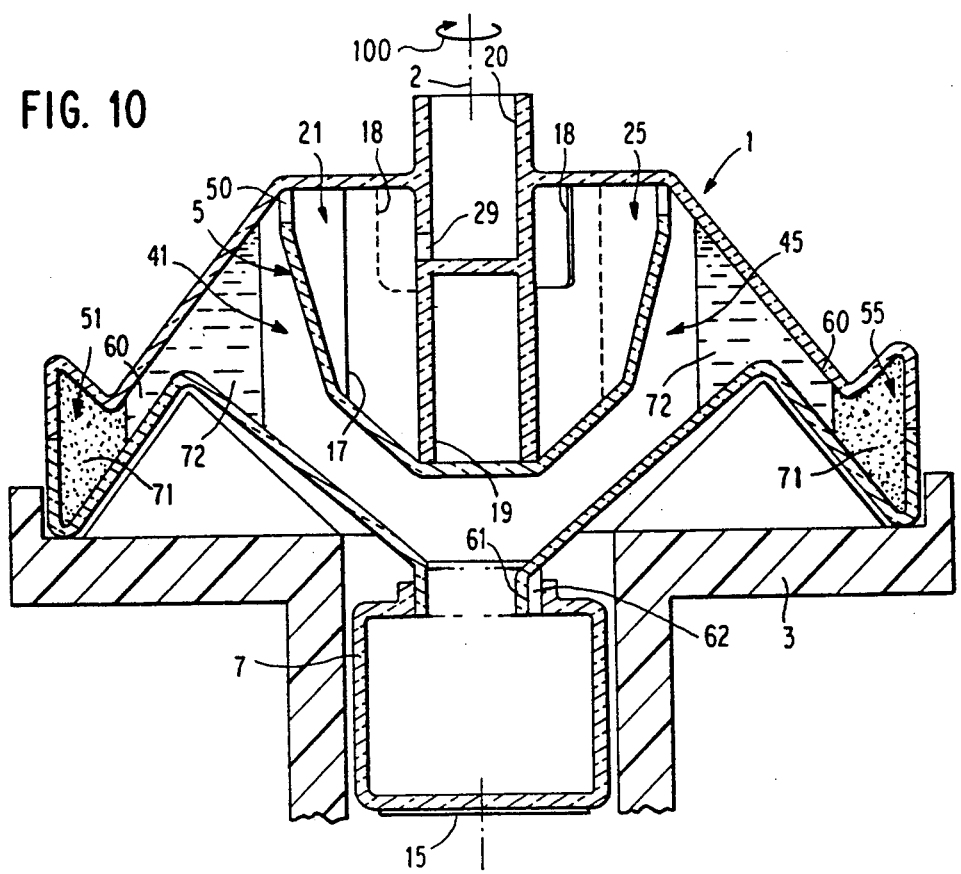
Figure 11:
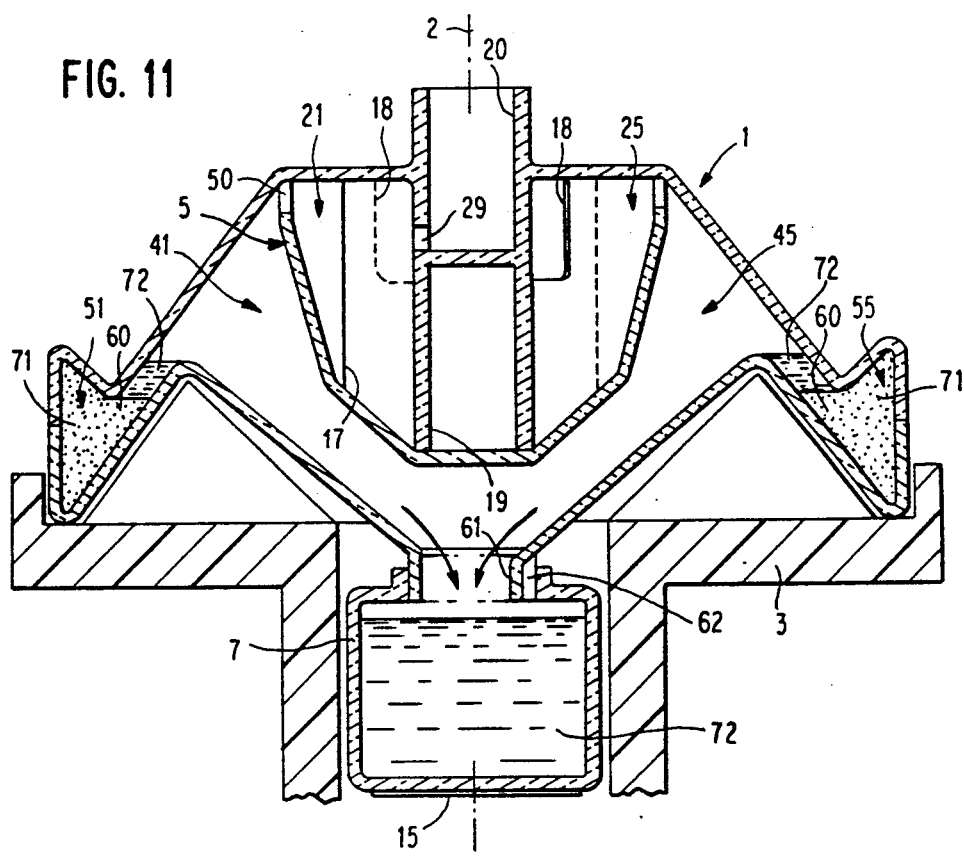

FIGS. 9 to 12 are diagrams showing the various operating stages of the apparatus 1. When the centrifuge is caused to spin about the axis 2 (arrow 100 in FIG. 9), the blood 70 is expelled from the compartments 21 to 28 via the orifices 50 (arrows 101). The red corpuscles 71 separate from the plasma 72 and are stored in the outer separation cells 51 to 58 (FIG. 10). When the centrifuge is stopped (FIG. 11) the red corpuscles 71 together with a very small quantity of plasma 72 are held captive in the outer cells 51 to 58 up to the level of the restrictions 60. The remainder of the plasma 72 pours under gravity into the funnel-shaped bottom portions of the receptacles 41 to 48 and thus enters the collector 7.

Figure 12:
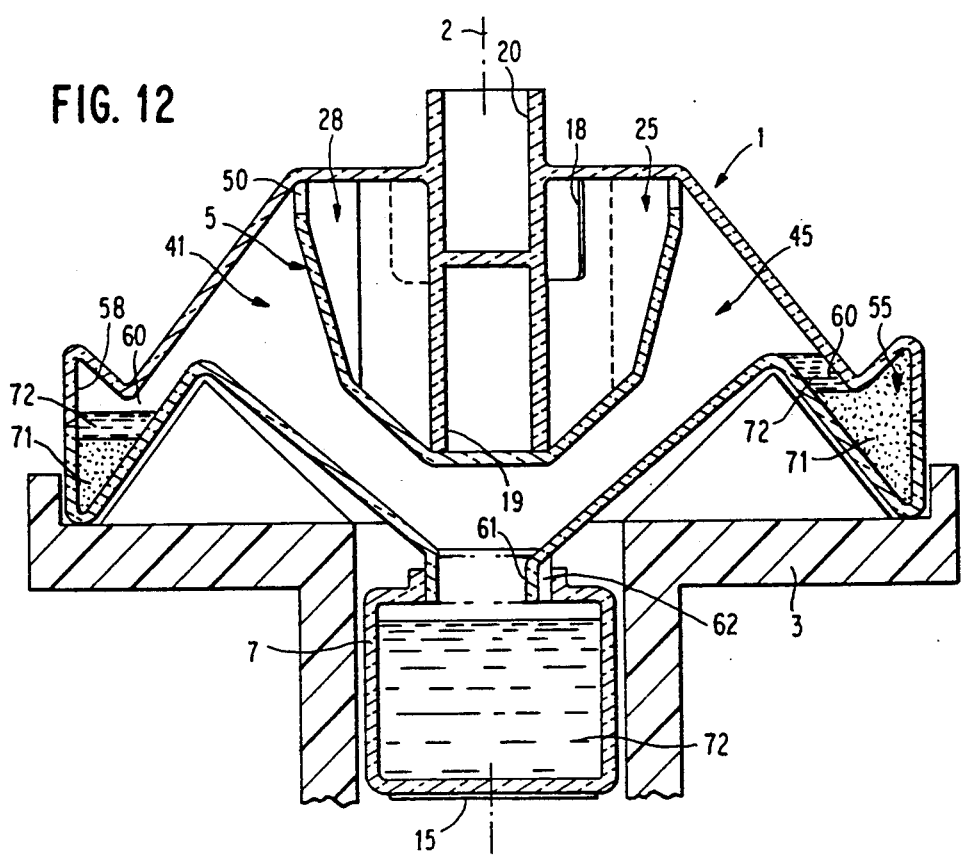

FIG. 12 shows the state of the cell 50 associated with the eighth compartment 28 after the centrifuge has stopped. The quantity of plasma 72 is insufficient to pass over the restriction 60 and it therefore remains inside the cell 58.

It can be seen that the structure of the apparatus of the invention and in particular the volumes of the various portions thereof are such that a small quantity of plasma may possibly be lost but under no circumstances do red corpuscles become mixed in with the plasma collected in the collector 7.

For a blood sample having a volume of about 6 milliliters (ml), the recovered quantity of plasma is about 2.2 ml.

The plasma collector 7 together with its identity marker 15 is disconnected from the other parts of the apparatus which are then discarded. The collector is then ready for sending to a laboratory for analysis if the analysis cannot be performed on the same premises as sampling and separation, otherwise it may be used on-site, e.g. by being integrated in an automatic machine.

Naturally, the invention is not limited to the embodiment described above. The number n may be different from eight. The apparatus 1 may be made up from a number of parts other than four, depending on the technology used.

The application of the apparatus of the invention is not limited to separating plasma and red corpuscles. The apparatus may be used for separating the two phases of any heterogeneous liquid so long as the volume fractions of the two phases are known and the volume proportions of the compartments and the outer cells are selected accordingly.

I claim:

1. Apparatus for separating two phases of a sample of heterogeneous liquid by centrifuging, the apparatus being particularly suitable for separating plasma from whole blood, wherein the apparatus comprises a closed assembly about an axis of revolution and comprising:

a distributor-divider disposed centrally and provided with n compartments delimited by radial partitions, the first compartment communicating firstly with the outside via a well for receiving a sample of whole blood and secondly with the second compartment via an overflow, the second compartment similarly communicating with a third via an overflow, and so on to the n-th compartment which does not communicate with the first compartment, all of the overflows being situated at the same height, and said distributor-divider being filled progressively merely under gravity;

a ring separator situated around said distributor-divider and incorporating n receptacles respectively communicating:

with n compartments via respective orifices situated at a height which is significantly greater than that of said overflows to ensure that the blood contained in said compartments pours into said receptacles only under the effect of centrifuging;

via respective restrictions with n outer separation cells for storing red corpuscles, the ratio of the volume to be contained in each cell relative to the volume of said associated compartment being not less than the volume ratio of red corpuscles relative to whole blood, thereby ensuring that the interface between the red corpuscles and the plasma which is established in each cell when centrifuging stops lies below said restriction;

in between, a common bottom portion narrowing into a funnel; and a removable plasma collector situated centrally beneath said funnel.

2. Apparatus according to claim 1, wherein said plasma collector includes identity means, with all of the necessary information being recorded at the moment that a sample is taken.

3. Apparatus according to claim 1, wherein said distributor-divider includes an (n+1)th compartment which is open to the outside and intended solely for disposing of any possible excess quantity of said sample.

4. Apparatus according to claim 1, wherein the apparatus is made of a plastic which is inert relative to blood.

* * * * *